United States Patent [19]
Gruter et al.

[11] Patent Number: 6,137,019
[45] Date of Patent: Oct. 24, 2000

[54] PROCESS FOR CONVERTING A GEMINALLY SUBSTITUTED CYCLOPENTADIENE

[75] Inventors: Gerardus J. M. Gruter, Maastricht; Johannes A. M. van Beek, Mountain View, both of Netherlands

[73] Assignee: DSM N.V., Heerlen, Netherlands

[21] Appl. No.: 09/180,179

[22] PCT Filed: Apr. 25, 1997

[86] PCT No.: PCT/NL97/00225

§ 371 Date: Mar. 3, 1999

§ 102(e) Date: Mar. 3, 1999

[87] PCT Pub. No.: WO97/42145

PCT Pub. Date: Nov. 13, 1997

[30] Foreign Application Priority Data

Apr. 25, 1997 [NL] Netherlands ............ 1003010

[51] Int. Cl.⁷ .............. C07C 2/02; C07C 7/20; C07C 5/22; C07C 5/27; C07F 9/02
[52] U.S. Cl. .............. 585/376; 585/1; 585/350; 585/671; 568/8; 568/77; 568/667; 564/460; 564/454; 564/464; 502/155; 502/103; 502/113; 502/117; 526/160; 526/161; 526/172

[58] Field of Search .............. 585/1, 350, 353, 585/375, 376, 671; 568/8, 77, 667; 564/460, 454, 464; 502/155, 103, 113, 117; 526/160, 161, 172

[56] References Cited

U.S. PATENT DOCUMENTS 5,648,578 7/1997 Layman et al. ............ 585/352

OTHER PUBLICATIONS

Jutzi, et al., "Dimethylaminoalkyl and Methoxyalkyl Substituted Tetramethylcyclopentadienes: Synthesis of Novel PolydentateLigands," Systhesis, No. 7 (Jul. 1993), 684–686.

Primary Examiner—Marian C. Knode
Assistant Examiner—Thuan D. Dang
Attorney, Agent, or Firm—Morrison & Foerster LLP

[57] ABSTRACT

Process for converting a geminally substituted cyclopentadiene containing 2–6 substituents into a non-geminally substituted cyclopentadiene by reacting the geminally substituted cyclopentadiene with a base, sodium or potassium at a temperature of 0–200° C. The invention also relates to mixtures of non-geminally substituted cyclopentadienes obtained by means of this process.

7 Claims, No Drawings

PROCESS FOR CONVERTING A GEMINALLY SUBSTITUTED CYCLOPENTADIENE

CROSS-REFERENCE TO RELATED APPLICATIONS

This application is the national state of PCT/NL97/00225, filed Apr. 25, 1997.

BACKGROUND OF THE INVENTION

1. Field of the Invention

The invention relates to a process for converting a geminally substituted cyclopentadiene containing 2–6 substituents into a non-geminally substituted cyclopentadiene.

2. Description of Related Art

Cyclopentadiene compounds, both substituted and unsubstituted, are used widely as a starting material for preparing ligands in metal complexes having catalytic activity. As metals in these complexes use is made in particular of transition metals and lanthanides.

A geminally substituted cyclopentadiene is a cyclopentadiene containing two substituents, which are not identical to a hydrogen atom, on the $sp^3$ carbon atom of the cyclopentadiene ring. These geminally substituted cyclopentadienes have the drawback that they cannot be converted into an aromatic anion by deprotonation. As a consequence, geminally substituted cyclopentadienes cannot be used as anionic ligand in the synthesis of metallocene catalysts.

Since direct alkylation of cyclopentadiene compounds is usually attended by geminal substitution (see Jutzi, Synthesis 1993, 684), there is a need for a process for converting a geminally substituted cyclopentadiene into a non-geminally substituted cyclopentadiene.

BRIEF DESCRIPTION OF THE INVENTION

It is the aim of the invention to provide this process.

The invention is characterized in that the geminally substituted cyclopentadiene is reacted with a base, sodium or potassium at a temperature of 0–200° C.

This ensures that the geminally substituted cyclopentadiene is converted into a non-geminally substituted cyclopentadiene.

For converting a geminally substituted cyclopentadiene into a non-geminally substituted cyclopentadiene, one of the substituents on the $sp^3$ carbon atom is to be removed or shifted (alkyl shift).

The process according to the invention provides a method for removing a substituent from the $sp^3$ carbon atom. For this, a C—C bond must be broken. Although C—H bond breakage is no exception during an organic synthesis, C—C bond breakage is very rare. Most of the examples of state of the art C—C bond breakage relate to C—C bond breakage in strained alkanes.

The geminally substituted cyclopentadiene may contain 2–6 substituents. At least two substituents should be present on the $sp^3$ carbon atom of the cyclopentadiene ring.

Preferably the geminally substituted cyclopentadiene contains 6 substituents.

Suitable substituents which can be split off via the process according to the invention are, for example, alkyl groups, linear as well as branched ones, and cyclic and aralkyl groups.

The methyl group is not suitable as substituent to be split off.

Besides carbon and hydrogen, the substituents may also comprise one or more hetero atoms from groups 14–17 of the Periodic System, for example O, N, Si or F. Examples of suitable groups are ethyl,(iso)propyl, secondary butyl, secondary pentyl, secondary hexyl and secondary octyl, (tertiary) butyl and higher homologues, cyclohexyl and 2-phenylethyl. Examples of substituents with hetero atoms from groups 15 and 16 of the Periodic System of the Elements are substituents according to the formula (R'$_n$D—R—), where R is a linking group
R' is a substituent,
D is a hetero atom from group 15 or 16 of the Periodic System of the Elements, and
n is the number of R' groups bound to D.

The R group forms the link between the Cp and the DR'$_n$ group.

The R' groups may each, separately, be a hydrocarbon radical containing 1–20 carbon atoms (such as alkyl, aryl, aralkyl, and the like). Examples of such hydrocarbon radicals are methyl, ethyl, propyl, butyl, hexyl, decyl, phenyl, benzyl, and p-tolyl. R' may also be a substituent which, in addition to or instead of carbon and/or hydrogen, contains one or more hetero atoms from groups 14–16 of the Periodic System of the Elements. Thus a substituent may be an N-, O-, and/or Si-containing group.

The R group may be a hydrocarbon group containing 1–20 carbon atoms (such as alkylidene, arylidene, arylalkylidene and the like). Examples of such groups are methylene, ethylene, propylene, butylene, phenylene, with or without a substituted side chain. Preferably, the R group has the following structure:

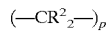

where p=1–4. The $R^2$ groups may each be H or a group as defined for R'.

The main chain of the R group may, in addition to carbon, also contain silicon or germanium.

The DR'$_n$ group consists of a hetero atom D, selected from group 15 or 16 of the Periodic System of the Elements, and one or more substituent(s) R' bound to D. The number of R' groups (n) is linked to the type of the hetero atom D, in the sense that n=2 if D is from group 15 and that n=1 if D is from group 16. Preferably, the hetero atom D is selected from the group consisting of nitrogen (N), oxygen (O), phosphorus (P) or sulphur (S); more preferably, the hetero atom is nitrogen (N). It is also preferred for the R' group to be an alkyl, more preferably an n-alkyl group containing 1–20C atoms.

Besides geminally substituted cyclopentadiene, use may also be made of mixtures that contain non-geminally substituted cyclopentadiene besides geminally substituted cyclopentadiene.

Preferably, one of the substituents on the $sp^3$ carbon atom in the cyclopentadiene ring is a substituent according to the above-mentioned formula (R'$_n$D—R—) and the other substituent an alkyl substituent, the alkyl substituent not being the same as methyl.

DETAILED DESCRIPTION OF THE INVENTION

The geminally substituted cyclopentadiene is converted into a non-geminally substituted cyclopentadienyl anion by reacting the geminally substituted cyclopentadiene with a base, sodium or potassium at a temperature of 0–200° C.

As base use can be made, for example, of organolithium compounds (RLi) or organomagnesium compounds (RMgX), where R is an alkyl, aryl or aralkyl group, and X is a halide, for example n-butyllithium or i-propylmagnesium chloride. Potassium hydride, sodium hydride, inorganic bases, for example NaOH and KOH, and alcoholates of Li, K and Na can likewise be used as a base. Mixtures of the above-mentioned compounds can also be used.

Preferably, sodium, potassium, potassium hydride, sodium hydride and the alcoholates of sodium and potassium are used. Special preference is given to the use of potassium or a mixture of sodium and potassium.

This reaction can be carried out in a polar dispersant, for example an ether. Examples of suitable ethers are tetrahydrofuran (THF), dimethoxyethane (DME) or dibutyl ether. A polar solvents such as, for example, toluene, can likewise be employed.

The reaction is carried out at a temperature of 0–200° C., preferably at a temperature of 60–120° C.

Usually the reaction is carried out at the boiling point of the dispersant used; for THF, for example, this is 67° C. and for dimethoxyethane (DME) 83° C.

The reaction with the base, sodium or potassium causes one of the substituents on the geminally substituted cyclopentadiene to be split off and a non-geminally substituted cyclopentadienyl anion to be formed.

If one of the substituents on the $sp^3$ carbon atom of the cyclopentadiene ring is a substituent according to the formula $(R'_nD—R—)$, where R is an ethylene group and D nitrogen, and the other substituent is an alkyl substituent (not methyl), then the alkyl substituent is selectively split off by the reaction.

However, even if one of the substituents on the $sp^3$ carbon atom of the cyclopentadiene ring does not have the form —$RDR'_n$, but if, for example, two alkyl groups (not both being methyl) are present, the reaction proceeds quantitatively and selectively. If two different alkyl groups are present, the selectivity is determined by the nature of the substituents.

In this manner substituted cyclopentadienes can be formed with the positions of the substituents being determined in advance.

If use is made of mixtures of geminally and non-geminally, m-fold substituted cyclopentadienes are used as starting compound then, after reaction with the base, sodium or potassium, mixtures of non-geminally substituted cyclopentadienyls are obtained. These mixtures contain two cyclopentadienyls, substituted to a mutually different degree of substitution, the degree of substitution of the one being m and that of the other m−1, where m=1–5. By degree of substitution is meant: the number of non-geminally substituents on the cyclopentadiene.

In this manner also mixtures of substituted cyclopentadienes with m and m−1 substituents are obtained, where m=2–5 and where at least one substituent is a substituent according to the formula —R—$DR'_n$ and the other substituents are alkyl and/or aralkyl substituents.

The above-mentioned mixtures can be separated after hydrolysis by means of distillation.

If mixtures of geminally substituted place isomers of cyclopentadiene are used as starting compound, then after reaction with the base, sodium or potassium mixtures of non-geminal positional isomers are obtained.

The resulting non-geminally substituted cyclopentadienes are highly suitable for use as a ligand in a metallocene catalyst.

It has been found that excellent catalysts can be obtained if the non-geminal Cp compounds, containing a substituent of the form $RDR'_n$ are used singly as a ligand on a metal which is not in its highest valency state. A mono-Cp-substituted metal complex of metals in a lower valency state than the highest possible is thus obtained, in which the Cp-containing ligand is monoanionic and has a strongly stabilizing effect without blocking the active sites of the complex, so that the complexes have excellent catalytic activity. In the non-geminal Cp compounds containing a substituent of the form $RDR'_n$, R is preferably an ethylene group.

Moreover, the non-geminal Cp compounds according to the invention are found to be able to stabilize highly reactive intermediaries such as organometal hydrides, boron hydrides, alkyls and cations. Furthermore the metal complexes containing the non-geminal Cp compounds according to the invention prove suitable as stable and volatile precursors for use in Metal Chemical Vapour Deposition.

In the synthesis of a metallocene catalyst use can also be made of mixtures of non-geminally substituted cyclopentadienes with m and m−1 substituents or mixtures of different position isomers, so that a mixture of catalysts with different ligands is formed.

Use of these catalyst mixtures in the polymerization of an olefin leads to the formation of polyolefin mixtures. An example of this is a bimodal polyolefin. This is a mixture of two polyolefins with different chain lengths.

The polymerization of α-olefins, for example ethylene, propylene, butene, hexene, octene and mixtures thereof and with dienes can be carried out in the presence of the metal complexes containing the cyclopentadienyl compounds according to the invention as a ligand. Particularly suitable for this purpose are the complexes of transition metals, not in their highest valency state, in which just one of the cyclopentadienyl compounds according to the invention is present as a ligand, and in which the metal is cationic during the polymerization. These polymerizations can be carried out in the manner known for this purpose, and the use of the metal complexes as a catalyst component does not require any significant adaptation of these processes. The known polymerizations are carried out in suspension, solution, emulsion, gas phase or as a bulk polymerization. It is customary to use, as a cocatalyst, an organometallic compound, the metal being selected from group 1, 2, 12 or 13 of the Periodic System of the Elements. Examples include trialkylaluminium, alkylaluminium halides, alkylaluminoxanes (such as methylaluminoxanes), tris (pentafluorophenyl) borate, dimethylanilinium tetra (pentafluorophenyl) borate or mixtures thereof. The polymerizations are carried out at temperatures between −50° C. and +350° C., more in particular between 25 and 250° C. Pressures used are generally between atmospheric pressure and 250 MPa, for bulk polymerizations more in particular between 50 and 250 MPa, for the other polymerization processes between 0.5 and 25 MPa. As dispersants and solvents use can be made, for example, of hydrocarbons such as pentane, heptane and mixtures thereof. Aromatic, optionally perfluorinated hydrocarbons likewise deserve consideration. The monomer to be employed in the polymerization can also be used as a dispersant or solvent.

The invention will be explained with reference to the following examples, but is not limited thereto.

EXAMPLES

Experimental

Dimethoxymethane was distilled from potassium-sodium alloy, benzophenone being used as indicator. The reactions were monitored by means of gas chromatography (GC type: Hewlett Packard 5890 Series II, equipped with autosampler type HP6890 Series Injector, integrator type HP3396A and HP Crosslinked Methyl Silicon Gum (25 m×0.32 mm×1.05 μm) column with one of the following temperature programmes: 50° C. (5 min.) rate: 7.5° C./min. 250° C. (29 minutes) or 150° C. (5 min.) rate: 7.5° C./min. 250° C. (29 minutes). The products were characterized using GC-MS (type Fisons MD800, equipped with a quadrupole mass detector, autoinjector Fisons AS800 and CPSi18 column (30 m×0.25 mm×1 μm, low bleed) with one of the following temperature programmes: 50° C. (5 min.) rate: 7.5° C./min. 250° C. (29 minutes) or 150° C. (5 min.) rate: 7.5° C./min. 250° C. (29 minutes) and NMR Bruker ACP200 ($^1$H=200 MHz.; $^{13}$C=50 MHz) or Bruker ARX400($^1$H=400 MHz.; $^{13}$C=100 MHz). Complexes were characterized using mass spectrometer Kratos MS80 or Finnigan Mat 4610.

Example I

Example IA

The preparation of tri(2-propyl)cyclopentadiene

In a double-walled reactor having a volume of 200 mL, provided with baffles, condenser, top stirrer, thermometer and dropping funnel, 180 g of clear 50% strength NaOH (2.25 mol), 9.5 g of Aliquat 336 (23 mmol) and 15 g (0.227 mol) of freshly cracked cyclopentadiene were combined. The reaction mixture was stirred turbulently at a speed of 1385 rpm for a few minutes. Then 84 g of 2-propyl bromide (0.68 mol) was added, cooling with water taking place at the same time. A few minutes after the addition of the first equivalent 2-propyl bromide (approx. 28 g) the temperature rose by approximately 10° C. After the reaction mixture started to cool (after a few minutes), the second equivalent 2-propyl bromide was added. The total metering time was 15 minutes. After this, the temperature rose slightly. After another few minutes, the remaining 2-propyl bromide was added. GC was used to show that 5–10 minutes after the addition of all the 2-propyl bromide (monosubstituted) 2-propylcyclopentadiene had been formed. The reaction mixture was then heated to 50° C. After 2 hours, stirring was stopped and phase separation was awaited. The water layer was drawn off, and 180 g (2.25 mol) of fresh 50% strength NaOH was added. Stirring then continued for one hour at 50° C. GC was used to show that at that instant between 90 and 95% of tri(2-propyl)cyclopentadiene was present in the mixture of di-, tri- and tetra-(2-propyl)cyclopentadiene. The product was distilled at 1.3 mbar and 77–78° C. After distillation, 31.9 g (0.166 mol; 73%) of tri(2-propyl) cyclopentadiene was obtained. Characterization took place with the aid of GC, GC-MS, $^{13}$C- and $^1$H-NMR.

Example IB

Conversion of 2,5,5-tri-(2-propyl)cyclopentadiene into potassium 1,3-di-(2-propyl)cyclopentadienyl 1.21 g (6.6 mmol) of tri(2-propyl)cyclopentadiene, as a mixture of van 2,5,5-tri-(2-propyl)cyclopentadiene (8%; geminal) and non-geminal double bond isomers (substitution pattern 1,2,4; 92%), was refluxed for 24 hours in a 100 mL three-necked flask in the presence of 2 equivalents potassium (13 mmol) in 50 mL of dimethoxyethane. After cooling, the residual potassium was removed, after which 1 mL of oxygen-free $D_2O$ was carefully added, with cooling. After standard upgrading, 1.11 g of a yellow oil was obtained. GCMS analysis showed that the reaction product was a mixture of di- and tri-(2-propyl)cyclopentadiene (1:9). D incorporation into all components present showed that all isomers of di- and tri-(2-propyl)cyclopentadiene are non-geminal. The reaction was highly selective and also complete. The identity of di-(2-propyl)cyclopentadiene was confirmed by comparing the spectroscopic data with di-(2-propyl) cyclopentadiene obtained independently via a different route.

Example II

Example IIA

In-situ preparation of 2-(N,N-dimethylaminoethyl) tosylate

Under dry nitrogen, a solution of n-butyllithium in hexane (321 mL; 1.65 mol/L; 529 mmol) was added (metering time: 60 minutes) at −10° C. to a solution of 2-dimethylaminoethanol (47.1 g; 529 mmol) in dry THF (1.5L) in a 5L three-necked round-bottomed flask provided with a magnetic stirrer and a dropping funnel. After the addition of all the butyllithium the mixture was brought to room temperature and stirred for 2 hours. Subsequently the mixture was cooled (−10° C.) and p-toluenesulphonyl chloride (101 g; 529 mmol) was added. This was followed by 15 minutes' stirring at this temperature, before the solution was added to a cyclopentadienyl anion.

Example IIB

Preparation of (dimethylaminoethyl)tri(2-propyl) cyclopentadiene

In a dry 500 mL three-necked flask with a magnetic stirrer, a solution of 62.5 mL of n-butyllithium (1.6M in n-hexane; 100 mmol) was added under a dry nitrogen atmosphere to a solution of 19.2 g (100 mmol) of tri-(2-propyl) cyclopentadiene in 250 mL of THF at −60° C. After heating to room temperature (in approximately 1 hour) stirring continued for a further 2 hours. After cooling to −60° C., a solution of (dimethylaminoethyl) tosylate (105 mmol) prepared in situ was added over a period of 5 minutes. The reaction mixture was heated to room temperature, followed by overnight stirring. The degree of conversion of the reaction was monitored by GC. After addition of water, the product was extracted with petroleum ether (40–60° C.). The combined organic layer was dried ($Na_2SO_4$) and evaporated under reduced pressure. The conversion was greater than 95%. 30% of the product is geminally substituted.

Example IIC

Conversion of geminal 1,3,5- and 2,3,5-tri-2-propyl(5-dimethylaminoethyl)cyclopentadiene into potassium 1,3- and 2,3-di-2-propyl(5-dimethylaminoethyl) cyclopentadienyl 1.71 g (6.5 mmol) of tri-(2-propyl)(dimethylaminoethyl) cyclopentadiene, as a mixture of geminal (30%) and non-geminal (70%) isomers, was refluxed for 24 hours in a 100 mL three-necked flask in the presence of 2 equivalents potassium (13 mmol) in 50 mL of dimethoxyethane. After cooling the residual potassium was removed, following which 1 mL of oxygen-free $D_2O$ was carefully added with cooling. After standard upgrading 1.50 g of a yellow oil was obtained. GCMS analysis showed that the reaction product was a mixture of di- and tri-(2-propyl)(dimethylaminoethyl) cyclopentadiene (3:7). D incorporation into all components present showed that all isomers of di- and tri-(2-propyl) (dimethylaminoethyl)cyclopentadiene are non-geminal. The reaction was highly selective and also complete. The identity of di-(2-propyl)(dimethylaminoethyl)cyclopentadiene was confirmed by comparing the spectroscopic data with di-(2- propyl)(dimethylaminoethyl)cyclopentadiene obtained independently via a different route.

Example III

Example IIIA

The preparation of tetra(ethyl)cyclopentadiene

A double-walled reactor with a volume of 1L, provided with baffles, cooler, top stirrer, thermometer and dropping funnel, was charged with 1050 g of clear 50% NaOH (13.1 mol), followed by cooling to 10° C. Subsequently, 32 g of Aliquat 336 (79 mmol) and 51 g of (0.77 mol) freshly cracked cyclopentadiene was added. The reaction mixture was stirred turbulently for a few minutes. Then, 344 g of ethylbromide (3.19 mol) was added over a period of one hour, cooling with water taking place at the same time. After stirring for 1 hour at room temperature, the reaction mixture was heated to 35° C., followed by stirring for another 6 hours. Stirring was stopped, and phase separation was awaited. The water layer was drawn off, and 1050 g (13.1 mol) of fresh 50% NaOH was added. Stirring was then continued for 5 hours at room temperature. By means of GC it was shown that at that instant 15% tri-, 78% tetra- and 7% penta(ethyl)cyclopentadiene were present in the mixture. The product was distilled at 11 mbar and 91° C. After distillation, 74.8 g (0.42 mol; 55%) of tetra(ethyl) cyclopentadiene was obtained. The product was characterized by means of GC, GC-MS, $^{13}$C- and $^1$H-NMR.

Example IIIB

Conversion of geminal 1,2,5,5- and 1,3,5,5-tetraethylcyclopentadiene into potassium 1,2,5- and 1,3,5-triethylcyclopentadienyl 1.21 g (6.8 mmol) of tetraethylcyclopentadiene, as a mixture of geminal (6%) and non-geminal isomers (94%), was refluxed for 24 hours in a 100 mL three-necked flask in the presence of 2 equivalents potassium (14 mmol) in 50 mL of dimethoxyethane. After cooling, the residual potassium was removed, following which 1 mL of oxygen-free $D_2O$ was carefully added with cooling. After standard upgrading 1.05 g of a yellow oil was obtained. GCMS analysis showed that the reaction product was a mixture of tri- and tetraethylcyclopentadiene (1:20). D incorporation into all components present showed that all isomers of tri- and tetraethylcyclopentadiene are non-geminal. The reaction was highly selective and also complete. The identity of triethylcyclopentadiene was confirmed by comparing the spectroscopic data with triethylcyclopentadiene obtained independently via a different route.

What is claimed is:

1. Process for converting a geminally substituted cyclopentadiene containing 2–6 substituents into a non-geminally substituted cyclopentadiene comprising reacting the geminally substituted cyclopentadiene with a base, sodium or potassium at a temperature of 0–200° C.

2. Process according to claim 1, wherein the geminally substituted cyclopentadiene contains 1 to 5 alkyl and/or arylalkyl substituents and at least one substituent according to the formula (—R—DR'$_n$), where R is a linking group containing 1–20 carbon atoms, D is heteroatom from group 15 or 16 of the Periodic System, R' is a hydrocarbon radical containing 1–20 carbon atoms, which may optionally contain one or more heteroatom from groups 14–16 of the Periodic System, and n is 1 or 2.

3. Process according to either claims 1 or 2 wherein the geminally substituted cyclopentadiene and non-geminally substituted cyclopentadiene are present as starting materials and the conversion results in a mixture of non-geminally substituted cyclopentadienes.

4. A mixture of two substituted cyclopentadienes comprising two substituted cyclopentadienes having mutually different degrees of substitution wherein one has a degree of substitution m and the other has a degree of substitution of m–1 wherein m is 2–5 and at least one substituent on one or both rings has a formula —R—DR'$_n$ and the other substituents are alkyl and/or arylalkyl substituents, wherein R is a linking group containing 1–20 carbon atoms, D is heteroatom selected from group 15 or 16 of the Periodic System, R' is a hydrocarbon radical containing 1–20 carbon atoms, which may optionally contain one or more heteroatoms from groups 14–16 of the Periodic System, and n is 1 or 2.

5. A mixture comprising position isomers of non-geminally substituted cyclopentadienes having m substituents, wherein m is 1–5 and at least one substituent has the formula (—R—DR'$_n$), and the other substituents are alkyl and/or arylalkyl substituents, where R is a linking group containing 1–20 carbon atoms, D is heteroatom selected from group 15 or 16 of the Periodic System, R' is a hydrocarbon radical containing 1–20 carbon atoms, which may optionally contain one or more heteroatoms selected from groups 14–16 of the Periodic and n is 1 or 2.

6. A mixture of transition metal catalysts comprising two types of metallocene catalysts characterized as having a transitional metal and a cyclopentadiene ligands, one with a m-fold substituted cyclopentadiene ligand and the other with a m–1 fold substituted cyclopentadiene ligand where the ligands are selected from the mixture of substituted cyclopentadienes according to either claims 4 or 5.

7. A process for preparing a polyolefin comprising polymerizing olefins in the presence of the catalyst mixture according to claim 6.

* * * * *